(12) United States Patent
Koram et al.

(10) Patent No.: US 7,204,130 B2
(45) Date of Patent: Apr. 17, 2007

(54) WINDSHIELD MOISTURE DETECTOR

(75) Inventors: Kwaku K. Koram, Wexford, PA (US); Allen R. Hawk, Freeport, PA (US); Shelby Chun, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 101 days.

(21) Appl. No.: 10/963,172

(22) Filed: Oct. 11, 2004

(65) Prior Publication Data

US 2005/0115308 A1    Jun. 2, 2005

Related U.S. Application Data

(63) Continuation-in-part of application No. 10/308,670, filed on Dec. 3, 2002, now Pat. No. 6,802,205.

(51) Int. Cl.
*G01N 5/02* (2006.01)
(52) U.S. Cl. .......................................... 73/73
(58) Field of Classification Search ................. 73/73, 73/74; 318/443, 444, 445, 446, 447, 448
See application file for complete search history.

(56) References Cited

U.S. PATENT DOCUMENTS

| | | | |
|---|---|---|---|
| 3,826,979 A | 7/1974 | Steinmann | 324/61 R |
| 4,100,398 A | 7/1978 | Levin | 219/541 |
| 4,323,726 A | 4/1982 | Criss et al. | 174/68.5 |
| 4,428,232 A | 1/1984 | Tanaka et al. | 73/304 C |
| 4,560,923 A | 12/1985 | Hanson | 324/61 QL |
| 4,703,237 A * | 10/1987 | Hochstein | 318/483 |
| 4,748,390 A | 5/1988 | Okushima et al. | 318/483 |
| 4,827,198 A | 5/1989 | Mueller et al. | 318/483 |
| 4,859,986 A * | 8/1989 | Van Auken et al. | 473/467 |
| 5,033,672 A | 7/1991 | Sakamoto et al. | 236/44 A |

(Continued)

FOREIGN PATENT DOCUMENTS

AU    6895194    2/1995

(Continued)

OTHER PUBLICATIONS

PCT Application Serial No. PCT/US02/06163 filed Feb. 28, 2002.

(Continued)

*Primary Examiner*—Jewel Thompson
(74) *Attorney, Agent, or Firm*—Andrew C. Siminerio

(57) ABSTRACT

A moisture detector can include a first elongated conductor disposed on a substrate. The first conductor can define a zigzag path between the opposite ends thereof. A second conductor can also be disposed on the substrate at least partially surrounding the first conductor. The second conductor can define between opposite ends thereof a zigzag path having a portion thereof that is positioned in substantially spaced parallel relation with the zigzag path of the first conductor along the sides thereof. A power conductor disposed on the substrate can be electrically connected to the first conductor intermediate the ends thereof via a gap defined between the ends of the second conductor. Ground conductors disposed on the substrate can be electrically connected to the ends of the second conductor. A temperature sensor can be utilized to correct the response of the moisture detector for temperature.

43 Claims, 6 Drawing Sheets

U.S. PATENT DOCUMENTS

| | | | |
|---|---|---|---|
| 5,598,146 A | 1/1997 | Schroder | 340/602 |
| 5,602,333 A | 2/1997 | Larrabee et al. | 73/149 |
| 5,653,904 A | 8/1997 | Adlparvar et al. | 219/203 |
| 5,659,294 A * | 8/1997 | Schroder | 340/602 |
| 5,661,303 A * | 8/1997 | Teder | 250/341.8 |
| 5,668,478 A * | 9/1997 | Buschur | 324/690 |
| 5,672,976 A | 9/1997 | Egger et al. | 324/668 |
| 5,682,788 A * | 11/1997 | Netzer | 73/73 |
| 5,694,012 A | 12/1997 | Pientka et al. | 318/444 |
| 5,703,568 A * | 12/1997 | Hegyi | 340/602 |
| 5,751,071 A | 5/1998 | Netzer | 307/10.1 |
| 5,780,718 A | 7/1998 | Weber | 73/29.01 |
| 5,780,719 A | 7/1998 | VanDam | 73/29.01 |
| 5,783,743 A * | 7/1998 | Weber | 73/29.01 |
| 5,801,307 A | 9/1998 | Netzer | 73/170.17 |
| 5,818,341 A | 10/1998 | Saurer et al. | 340/602 |
| 5,900,821 A | 5/1999 | Petzold | 340/604 |
| 5,990,647 A | 11/1999 | Zettler | 318/483 |
| 6,052,196 A | 4/2000 | Pientka et al. | 356/445 |
| 6,066,933 A | 5/2000 | Ponziana | 318/483 |
| 6,084,519 A | 7/2000 | Coulling et al. | 340/602 |
| 6,094,981 A | 8/2000 | Hochstein | 73/170.17 |
| 6,118,383 A | 9/2000 | Hegyi | 340/602 |
| 6,207,967 B1 | 3/2001 | Hochstein | 250/574 |
| 6,218,741 B1 | 4/2001 | Braun et al. | 307/10.1 |
| 6,232,603 B1 | 5/2001 | Nelson | 250/339.11 |
| 6,250,148 B1 | 6/2001 | Lynam | 73/170.17 |
| 6,262,407 B1 | 7/2001 | Teder | 250/205 |
| 6,262,410 B1 | 7/2001 | Stam et al. | 250/208.1 |
| 6,268,612 B1 | 7/2001 | Teder | 250/574 |
| 6,313,457 B1 | 11/2001 | Bauer et al. | 250/214 C |
| 2002/0189329 A1 | 12/2002 | Wimmer | |

FOREIGN PATENT DOCUMENTS

| | | |
|---|---|---|
| DE | 101 27 978 | 11/2002 |
| DE | 101 27 990 | 12/2002 |
| DE | 101 28 010 | 1/2003 |
| EP | 0 308 990 | 3/1989 |
| EP | 0 638 822 | 2/1995 |
| EP | 0 890 143 B1 | 12/2001 |
| EP | 1 264 746 | 5/2002 |
| JP | 55063940 A | 5/1980 |
| JP | 04184226 A | 7/1992 |
| JP | 09043187 | 2/1997 |
| WO | WO98/30922 | 7/1998 |
| WO | 01/81931 A1 | 11/2001 |
| WO | WO2004/050442 | 6/2004 |
| WO | 2005/029134 A1 | 3/2005 |

OTHER PUBLICATIONS

International Search Report mailed Sep. 9, 2004.

* cited by examiner

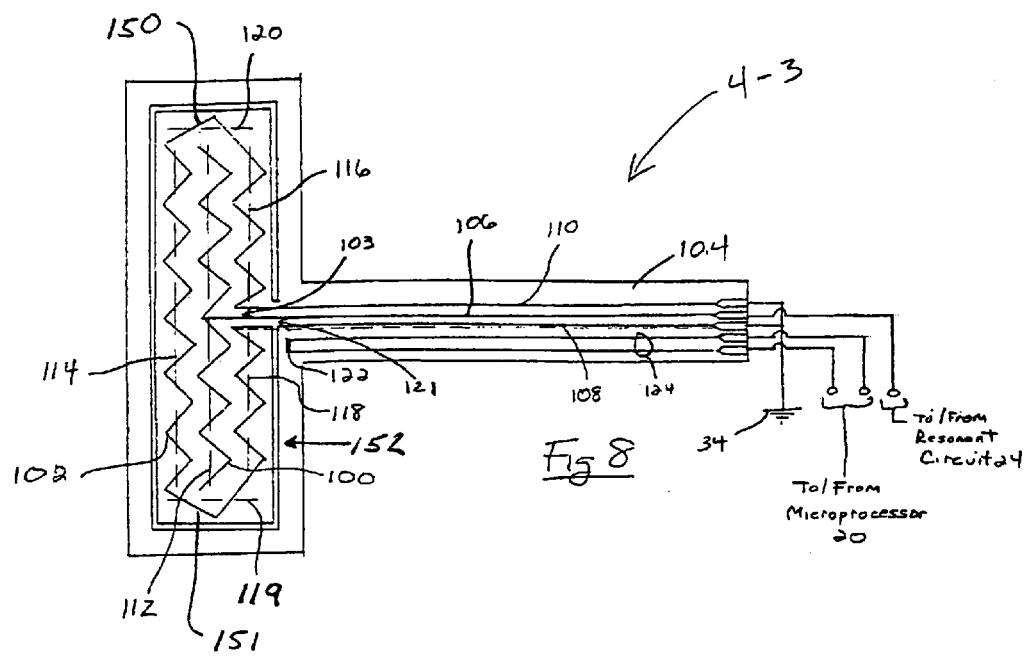
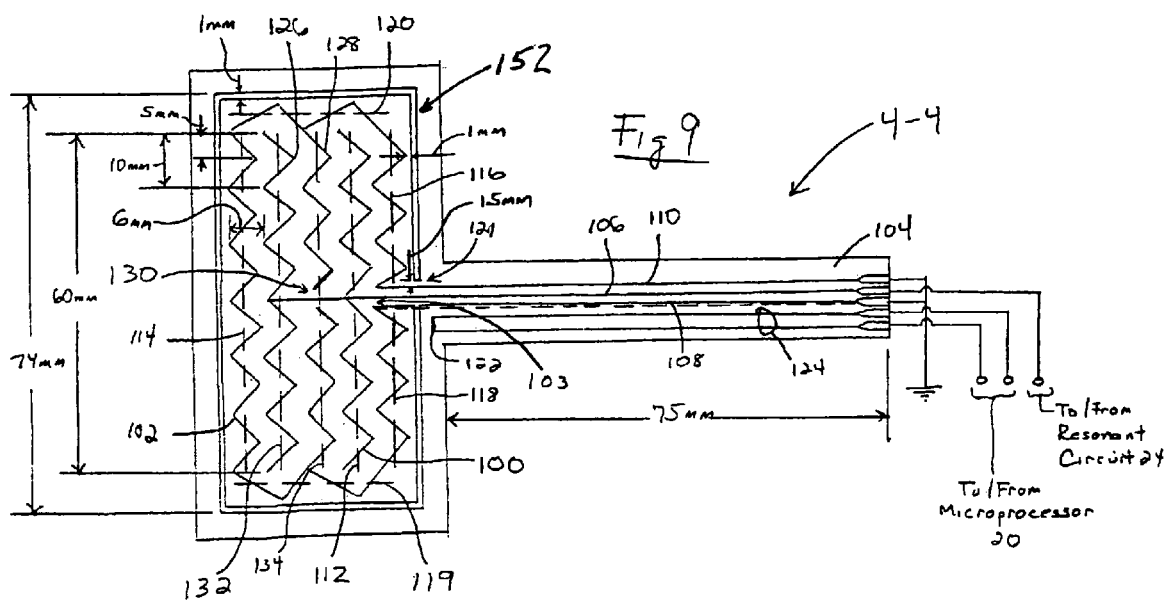

WINDSHIELD MOISTURE DETECTOR

CROSS REFERENCE TO RELATED APPLICATION

This application is a continuation-in-part of U.S. patent application Ser. No. 10/308,670, filed Dec. 3, 2002 now U.S. Pat. No. 6,802,205, which is incorporated herein by reference.

BACKGROUND OF THE INVENTION

1. Field of the Invention

The present invention relates to moisture detection and, more particularly, to moisture detection on a vehicle windshield.

2. Description of the Prior Art

Heretofore, the detection of moisture on a windshield of a vehicle was accomplished in four basic manners: capacitive sensor systems, resistive sensor systems, ultrasonic sensor systems and optical sensor systems.

A capacitive sensor system includes a capacitor formed on the windshield. In response to moisture on the windshield, the capacitance of the capacitor changes. A sensing circuit is connected to detect the changing capacitance and to control the operation of a windshield wiper as a function of the changing capacitance. Examples of capacitive moisture sensors include U.S. Pat. No. 5,668,478 to Buschur; U.S. Pat. No. 5,682,788 to Netzer; U.S. Pat. No. 5,801,307 to Netzer; and U.S. Pat. No. 6,094,981 to Hochstein.

A resistive measurement system includes two conductive elements disposed in spaced relation on the windshield, or another part of the vehicle, such as a conventional whip antenna. Circuitry coupled to the conductive elements measures a change in resistance thereof in response to water bridging the resistive elements and controls the operation of the windshield wiper as a function of the change in resistance. Examples of resistive measurement systems include U.S. Pat. No. 5,659,294 to Schroder; U.S. Pat. No. 5,598,146 to Schroder; U.S. Pat. No. 5,780,718 to Weber; U.S. Pat. No. 5,780,719 to VanDam; U.S. Pat. No. 5,783,743 to Weber; and U.S. Pat. No. 5,900,821 to Petzold.

An ultrasonic sensor system includes a transducer that emits an ultrasonic signal toward a first face of a sheet and receives a reflected ultrasonic signal on a second face of the sheet. The variation in the reflected signal is utilized to determine the presence or absence of foreign bodies on the second face of the sheet. Examples of ultrasonic sensor systems include U.S. Pat. No. 5,818,341 to Saurer et al. and European Publication No. EP0638822.

An optical sensor system includes a light detector positioned to detect light reflected off a windshield from a light source. In response to the presence of moisture on the windshield, the amount of light detected by the light sensor will change due to changing reflection of the light from the light source, thus causing a change in the output of the light sensor. Detecting circuitry detects the change in output from the light detector in response to the change in light impinging thereon and operates the windshield wiper as a function of the change. Examples of light detecting systems include U.S. Pat. No. 5,694,012 to Pientka et al.; U.S. Pat. No. 5,990,647 to Zettler; U.S. Pat. No. 6,052,196 to Pientka et al.; U.S. Pat. No. 6,066,933 to Ponziana; U.S. Pat. No. 6,084,519 to Coulling et al.; U.S. Pat. No. 6,207,967 to Hochstein; U.S. Pat. No. 5,661,303 to Teder; U.S. Pat. No. 6,250,148 to Lynam; U.S. Pat. No. 6,218,741 to Braun et al.; and U.S. Pat. No. 6,232,603 to Nelson.

A problem with a capacitive sensor system includes the need to form a capacitor having sufficient capacitance whereupon the change in capacitance in response to the presence of rain on the windshield can be detected by suitable detection circuitry. Another problem with a capacitive sensor system is the change in capacitance due to heating or cooling of the metal films forming the capacitor thereby resulting in a change in the capacitance of the capacitor during use.

A problem with a resistive sensor system includes the need to have the resistive elements formed on the outer surface of the windshield whereupon the resistive elements are exposed to weather and possible deterioration. In addition, the resistive elements of a resistive sensor system are also subject to changes in resistance due to changes in the temperature.

A problem with an ultrasonic sensor system and an optical sensor system includes the need to position the transducer of the ultrasonic sensor system and the light transmitter and light receiver of the optical sensor system inside the vehicle to detect the presence of moisture at a suitable location on the windshield. However, positioning the ultrasonic sensor system or the optical sensor system at a suitable location on the windshield often results in partially blocking a drivers view through the windshield or in the positioning of such sensor system at less than an optimal location for detecting the presence of moisture on the windshield. Moreover, the sensitivity of an optical sensor to detect moisture can be compromised by the color or shade of the windshield in the path of the light propagating from the light transmitter to the light receiver.

It would, therefore, be desirable to provide a small, nearly invisible, moisture detector disposed on either a flexible substrate that is coupled to a sheet, such as a windshield, or on the sheet itself. The moisture detector can be coupled to circuitry for stimulating the moisture detector and circuitry for detecting a change in a characteristic of the moisture detector due to the presence of moisture on the sheet. It would also be desirable to provide a method for detecting the change of the characteristic of the moisture detector as a function of the temperature of the sheet.

SUMMARY OF THE INVENTION

The invention is a moisture detector that includes a first elongated conductor disposed on a substrate. The first conductor defines a path comprising multiple electric field emitting points, e.g. a zigzag path, between opposite ends thereof. A second elongated conductor is disposed on the substrate at least partially surrounding the first conductor. The second conductor defines between opposite ends thereof a zigzag path having a portion thereof that is positioned in substantially spaced parallel relation with the zigzag path of the first conductor along the sides thereof.

A power conductor can be disposed on the substrate and electrically connected to the first conductor intermediate the ends thereof via a gap defined between the ends of the second conductor. A ground conductor can be disposed on the substrate and electrically connected to one end of the second conductor. Another ground conductor can also be disposed on the substrate and electrically to the other end of the second conductor.

Portions of the second conductor can be spaced from opposite ends of the first conductor and can define mirror image zigzag paths.

The ground conductor can at least partially surround the second conductor. The ground conductor can define a gap for passage of the power conductor for electrical connection to the first conductor.

A third elongated conductor can be disposed on the substrate between the first and second conductors. The third conductor can define between opposite ends thereof a zigzag path that is positioned in substantially spaced parallel relation with the zigzag path of the first conductor. A fourth elongated conductor can be disposed on the substrate between the first and third conductors. The fourth conductor can define between opposite ends thereof a zigzag path that is positioned in substantially spaced parallel relation with the zigzag path of the first conductor. The fourth conductor can also define a gap intermediate the ends thereof that are coupled to the second conductor. The power conductor can be electrically connected to the third conductor intermediate the ends thereof via the gap defined intermediate the ends of the fourth conductor.

The substrate can be a windshield having a plurality of transparent sheets laminated together or a flexible substrate configured to be disposed between the transparent sheets of the windshield. A temperature sensor can be disposed in operative relation to the plurality of conductors.

The invention is also a moisture detector that includes a first conductor disposed on a substrate, a second conductor disposed on the substrate at least partially surrounding the first conductor whereupon a gap is defined between the ends of the second conductor, a power conductor disposed on the substrate and electrically connected to the first conductor via the gap between the ends of the second conductor, and a ground conductor disposed on the substrate and electrically connected to one end of the second conductor.

The first conductor can define a longitudinal axis and at least a portion of the second conductor can define a longitudinal axis that is positioned in substantially spaced parallel relation with the longitudinal axis of the first conductor.

The conductors can define zigzag paths along their longitudinal axes. The zigzag paths of the conductors can track each other in substantially spaced parallel relation along their longitudinal axes.

Portions of the second conductor can be spaced from opposite ends of the first conductor and can define longitudinal axes that are positioned substantially perpendicular to the longitudinal axis of the first conductor. These portions of the second conductor can define mirror image zigzag paths.

The ground conductor can at least partially surround the second conductor and can define a gap for passage of the power conductor for electrical connection to the first conductor.

A third conductor can be disposed on the substrate between the first and second conductors. A fourth conductor can be disposed on the substrate between the first and third conductors. The fourth conductor can define a gap intermediate the opposite ends thereof that are coupled to the second conductor. The power conductor can be electrically connected to the third conductor via the gap intermediate the ends of the fourth conductor.

The first conductor can define a longitudinal axis and at least a portion of the second conductor can define a longitudinal axis that is positioned in substantially spaced parallel relation with the longitudinal axis of the first conductor. The third and fourth conductors can define longitudinal axes that are positioned in substantially spaced parallel relation with the longitudinal axis of the first conductor. The conductors can define along their longitudinal axes zigzag paths that track each other in substantially spaced parallel relation along their longitudinal axes.

The ground conductor can at least partially surround the second conductor and can define a gap for passage of the power conductor for electrical connection to the first and third conductors.

The invention is also a method of moisture detection comprising (a) providing a moisture detector on a substrate; (b) providing a temperature sensor in operative relation to the moisture detector; (c) measuring a property of the moisture detector that varies in response to an amount of moisture present adjacent the moisture detector; (d) measuring a property of the temperature sensor that varies in response to the temperature adjacent the moisture detector; and (e) causing a system to operate as a function of the measured properties of the moisture detector and the temperature sensor.

The invention is also a moisture detection system that includes a moisture detector disposed on a substrate; a temperature sensor disposed in operative relation to the moisture detector for measuring a temperature on or adjacent the moisture detector; means for measuring a property of the moisture detector that varies in response to an amount of moisture present adjacent the moisture detector; means for measuring a property of the temperature sensor that varies in response to the temperature on or adjacent the moisture detector; and means for causing a system to operate as a function of the measured properties of the moisture detector and the temperature sensor.

The substrate can be a windshield and the system can be a windshield wiper system.

The measured property of the temperature sensor can be a resistance of a thermistor acting as the temperature sensor, a potential output by a bi-metallic junction acting as the temperature sensor, a resistance of a conductor acting as the temperature sensor or a signal output by an optical temperature sensor acting as the temperature sensor.

Lastly, the invention is a moisture detector that includes a plurality of conductors disposed on a substrate and defining along their longitudinal axes zigzag paths that track each other in substantially spaced parallel relation; a power conductor disposed on the substrate and electrically connected to a first conductor of the plurality of conductors; and a ground conductor disposed on the substrate and electrically connected to a second conductor of the plurality of conductors.

The second conductor can at least partially surround the remaining plurality of conductors and can define a gap between the ends of the second conductor. The power conductor can be electrically connected to the first conductor via the gap between the ends of the second conductor.

Portions of the second conductor spaced from opposite ends of the first conductor can define longitudinal axes that are positioned substantially perpendicular to the longitudinal axis of the first conductor. These portions of the second conductor can define mirror image zigzag paths.

The plurality of conductors can include a third conductor positioned between the first and second conductors. The plurality of conductors can also include a fourth conductor positioned between the first and third conductors. The fourth conductor can define a gap intermediate the ends thereof that are electrically connected to the ground conductor. The power conductor can be electrically connected to the third conductor via the gap intermediate the ends of the fourth conductor.

The substrate can be a windshield having a plurality of transparent sheets laminated together or a flexible substrate configured to be disposed between the transparent sheets of the windshield. A temperature sensor can be disposed in operative relation to the plurality of conductors.

BRIEF DESCRIPTION OF THE DRAWINGS

FIG. 8 is a plan view similar to that shown in FIG. 5 of a third nonlimiting embodiment of a moisture detector for detecting moisture on a sheet incorporating features of the present invention;

FIG. 9 is a plan view similar to that shown in FIG. 5 of a fourth nonlimiting embodiment of a moisture detector for detecting moisture on a sheet incorporating features of the present invention;

DETAILED DESCRIPTION OF THE INVENTION

Figure 1:
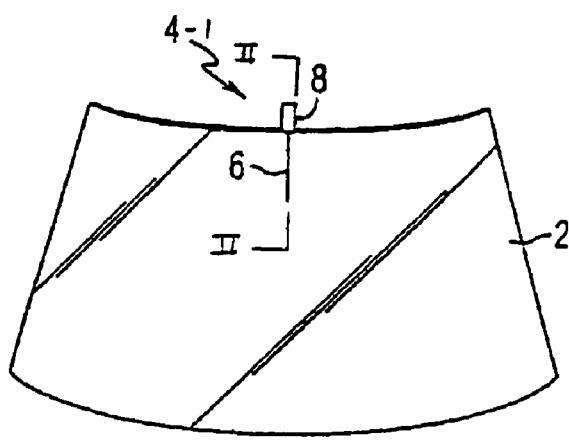
FIG. 1 is a plan view of a sheet, such as a sheet of glass or a windshield, including a first nonlimiting embodiment of a moisture detector for detecting moisture on the sheet incorporating features of the present invention.

The present invention will be described with reference to the accompanying figures where like reference numbers correspond to like elements.

As used herein, spatial or directional terms, such as "inner", "outer", "left", "right", "up", "down", "horizontal", "vertical", and the like, relate to the invention as it is shown in the drawing figures. However, it is to be understood that the invention can assume various alternative orientations and, accordingly, such terms are not to be considered as limiting. Further, all numbers expressing dimensions, physical characteristics, and so forth, used in the specification and claims are to be understood as being modified in all instances by the term "about". Accordingly, unless indicated to the contrary, the numerical values set forth in the following specification and claims can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, and all subranges in between. Also, as used herein, terms such as "positioned on" or "supported on" mean positioned or supported on but not necessarily in direct surface contact with. For example, a substrate "positioned on" a glass sheet does not preclude the presence of one or more other materials located between the substrate and the surface of the sheet.

With reference to FIG. 1, a sheet or panel of optically transparent material, such as a sheet of glass or a vehicle windshield 2, includes a moisture detector 4 disposed thereon or incorporated therein. In a first nonlimiting embodiment of the present invention, moisture detector 4-1 includes one or more electrical conductors 6 connected to a connector, e.g. conductive foil 8, which is utilized for connecting electronic circuitry to electrical conductor 6. In the nonlimiting embodiment shown in FIG. 1, foil 8 is shown extending outside the periphery of windshield 2. However, this is not to be construed as limiting the invention since foil 8 may be disposed entirely within the periphery of windshield 2.

Figure 2:
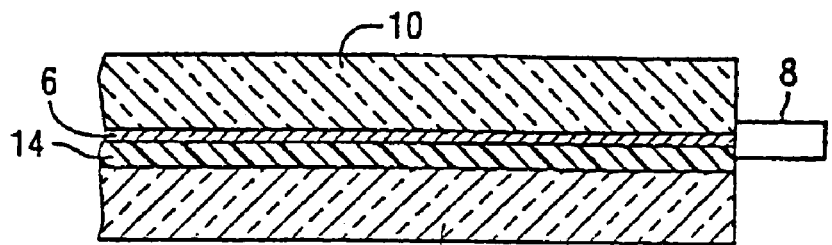
FIG. 2 is a cross section taken along lines II—II in FIG. 1.

With reference to FIG. 2, and with continuing reference to FIG. 1, windshield 2 is desirably formed by outer and inner glass plies 10 and 12 bonded together by a plastic interlayer 14, such as polyvinylbutyral, to form windshield 2 as a unitary structure. Plies 10 and 12, however, may be other transparent rigid material, such as but not limited to polycarbonate. Each electrical conductor 6 can be disposed on an inward or an outward facing surface of glass ply 10 or glass ply 12. Each electrical conductor 6 can be a conductive wire or sheet, or a conductive coating applied to one of the surfaces of glass ply 10 or glass ply 12 in the form of a line or a sheet, or a dispersion of electrically conductive particles applied to one of the surfaces of glass ply 10 or glass ply 12 in the form of a line or a sheet. Although not required, each electrical conductor 6 has a width and/or thickness that render it not easily discernable to the naked eye. In one nonlimiting embodiment of the invention, the width of the electrical conductors 6 is no greater than 0.35 mm, for example no greater than 0.30 mm or no greater than 0.25 mm.

Figure 3:
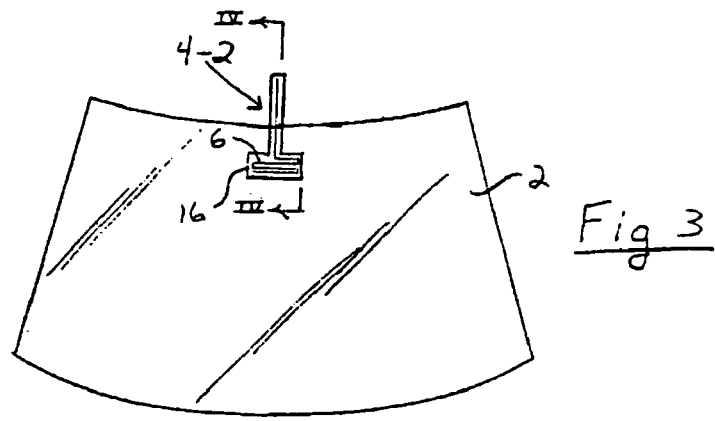
FIG. 3 is a plan view of a sheet, such as a sheet of glass or a windshield, including a second nonlimiting embodiment of a moisture detector for detecting moisture on the sheet incorporating features of the present invention.
Figure 4:
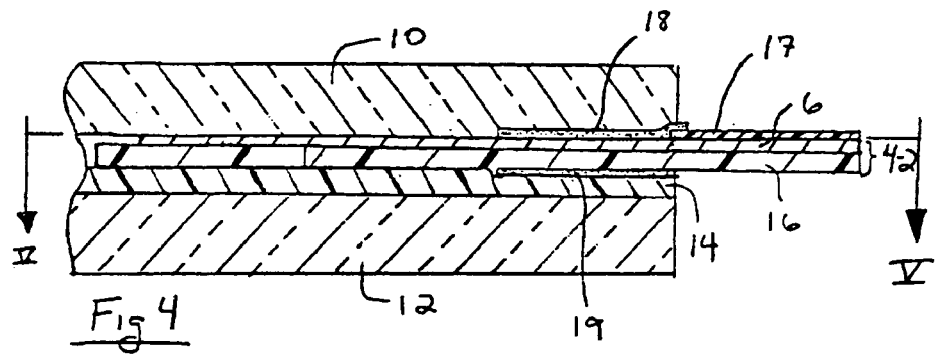
FIG. 4 is a cross section taken along lines IV—IV in FIG. 3.
Figure 5:
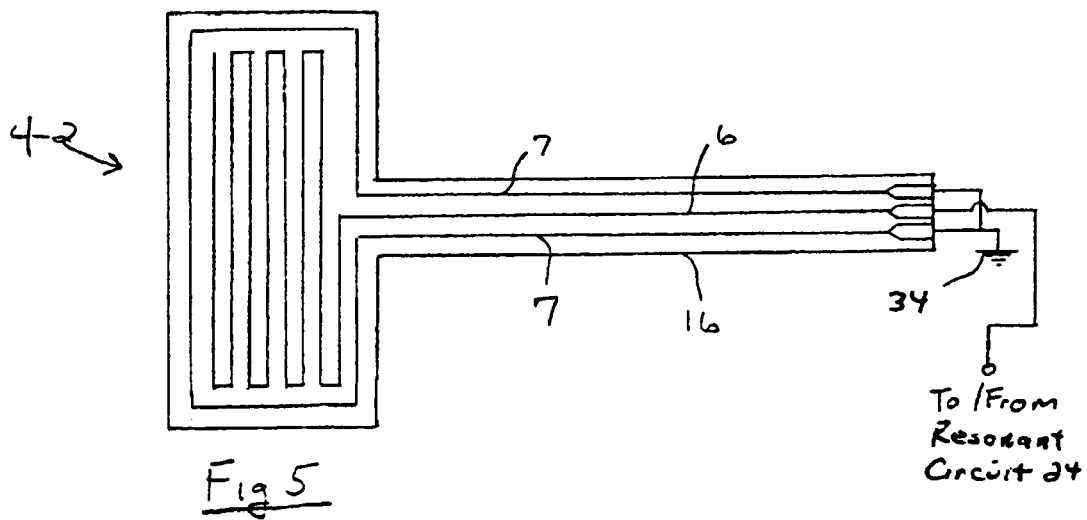
FIG. 5 is a view taken along lines V—V in FIG. 4, with portions removed for clarity.

With reference to FIGS. 3–5, in a second nonlimiting embodiment, moisture detector 4-2 includes one or more electrical conductors 6 disposed on a flexible substrate 16. In FIGS. 3 and 4, part of flexible substrate 16 including electrical conductor(s) 6 disposed thereon extends outside the periphery of windshield 2 to facilitate connection of electronic circuitry to electrical conductor(s) 6. However, this is not to be construed as limiting the invention since flexible substrate 16 having electrical conductor(s) 6 disposed thereon may be disposed entirely within the periphery of windshield 2.

As shown in FIG. 4, flexible substrate 16 can be sandwiched between glass plies 10 and 12 with electrical conductor 6 facing an inward facing surface of glass ply 10 or glass ply 12, or one of the outward facing surfaces of plastic interlayer 14. Alternatively, flexible substrate 16 can be disposed on an outward facing surface of glass ply 10 or glass ply 12 with electrical conductor 6 facing toward or away from said outward facing surface. As another alternative, the flexible substrate 16 can be incorporated within the interlayer 14. Although not required, to avoid undesirable exposure of flexible substrate 16 and/or electrical conductor(s) 6, it is desirable to position flexible substrate 16 between glass plies 10 and 12 versus positioning flexible substrate 16 on an outward facing surface of glass ply 10 or glass ply 12.

Flexible substrate 16 can be formed from any suitable flexible and insulative material, such as but not limited to polyethyleneterephthalate (PET), polyvinylbutyral (PVB), ultra-thin glass, etc. In one nonlimiting embodiment, substrate 16 is 2 mil thick PET. A desired pattern of electrical conductor(s) 6 can be formed from a sheet of any suitable electrically conductive material adhered to flexible substrate 16 utilizing conventional photolithographic processing techniques. The desired pattern of electrical conductor(s) 6 can also be formed on flexible substrate 16 by screen printing a suitable conductive material in the desired pattern on flexible substrate 16 or by ink jetting a suitable conductive material in the desired pattern on flexible substrate 16. The desired pattern of electrical conductor(s) 6 can also be formed on flexible substrate 16 by a wire, such as but not limited to copper wire, secured to or embedded within the substrate 16. Although not required, in one nonlimiting embodiment, the wire has a small diameter so that the wire is less visible in the windshield 2. In one nonlimiting embodiment, the wire is 36 AWG tin plated copper wire. As discussed above, it should be appreciated that rather than using a flexible substrate, the conductors 6 can be applied directly to a surface of the glass plies or interlayer. For example, and without limiting the present invention, rather than combining the wire with the substrate 16, the wire can be secured to or embedded within the interlayer 14. The foregoing methods of forming the pattern of electrical conductor(s) 6 on flexible substrate 16 are not to be construed as limiting the invention since the use of any suitable means for forming the desired pattern of electrical conductor(s) 6 on flexible substrate 16 is envisioned.

Figure 6:
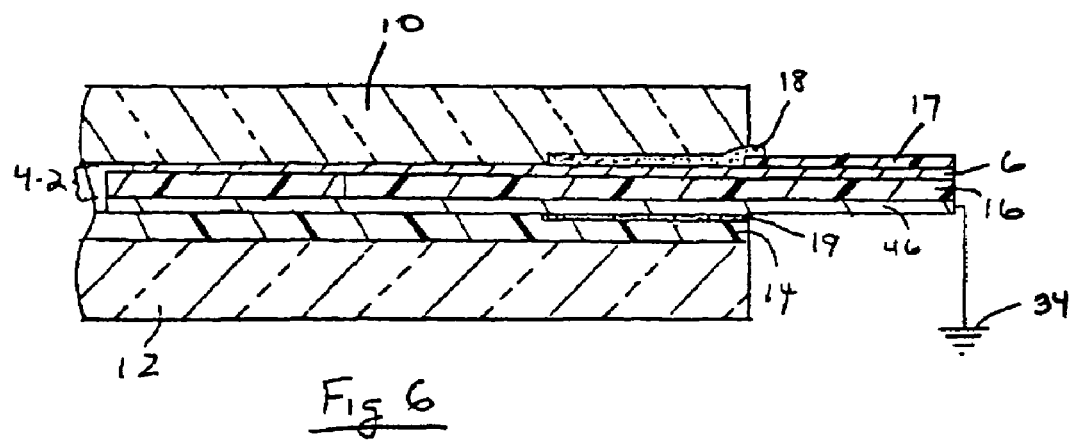
FIG. 6 is a cross section of the second embodiment moisture detector shown in FIG. 4 including a conductive material positioned on a side of the substrate opposite the electrical conductor.

With reference to FIGS. 5 and 6, and with continuing reference to FIGS. 3 and 4, the portion of flexible substrate 16 extending outside the periphery of windshield 2 can have electrical conductor(s) 6 sandwiched between flexible substrate 16 and an insulative material 17 adhered to electrical conductor(s) 6. Insulative material 17 can be formed from a sheet of suitable insulative material, such as Kapton® polyimide film (a registered trademark of E.I. DuPont de Nemoirs and Company Corporation, Wilmington, Del.), or any other suitable solid or flowable insulative material that acts to protect electrical conductor(s) 6. Since the portions of electrical conductor(s) 6 and substrate 16 sandwiched between glass plies 10 and 12 are protected thereby from moisture and/or particulate contaminants, an end of insulative material 17 can terminate between glass plies 10 and 12.

To avoid exposure of electrical conductor(s) 6 sandwiched between glass plies 10 and 12 to moisture and/or particulate contaminates, a thermoset adhesive 18 can be disposed on the electrical conductor 6 side of flexible substrate 16 positioned between glass plies 10 and 12. This thermoset adhesive 18 covers the end of insulative material 17 sandwiched between glass plies 10 and 12 and extends between glass plies 10 and 12 a sufficient distance so that when it is cured, thermoset adhesive 18 forms with glass plies 10 and 12 and plastic interlayer 14 a hermetic seal that inhibits moisture and/or particulate contaminates from contacting the portion of electrical conductor(s) 6 sandwiched between glass plies 10 and 12.

A pressure sensitive adhesive 19 can be disposed between flexible substrate 16 and plastic interlayer 14 for securing the position of flexible substrate 16 between glass plies 10 and 12 prior to exposing thermoset adhesive 18 and plastic interlayer 14 to a curing heat.

As shown in FIG. 5, flexible substrate 16 can include a ground conductor 7 that at least partially surrounds electrical conductor(s) 6. Connecting ground conductor 7 to an external reference voltage 34, such as ground, forms a ground loop around electrical conductor(s) 6. This ground loop avoids undesirable electromagnetic interference from affecting the operation of electrical conductor(s) 6 acting as a resonating element of moisture detector 4-2. Moreover, as shown in FIG. 6, a side of flexible substrate 16 opposite electrical conductor(s) 6 can also or alternatively include a conductive material 46 disposed thereon that can be connected to external reference voltage 34. Conductive material 46 can be in the form of a sheet, one or more lines, a mesh, or any other suitable form that defines a faraday shield that avoids undesirable electromagnetic interference from affecting the operation of electrical conductor(s) 6 acting as the resonating element of moisture detector 4-2.

Figure 7:
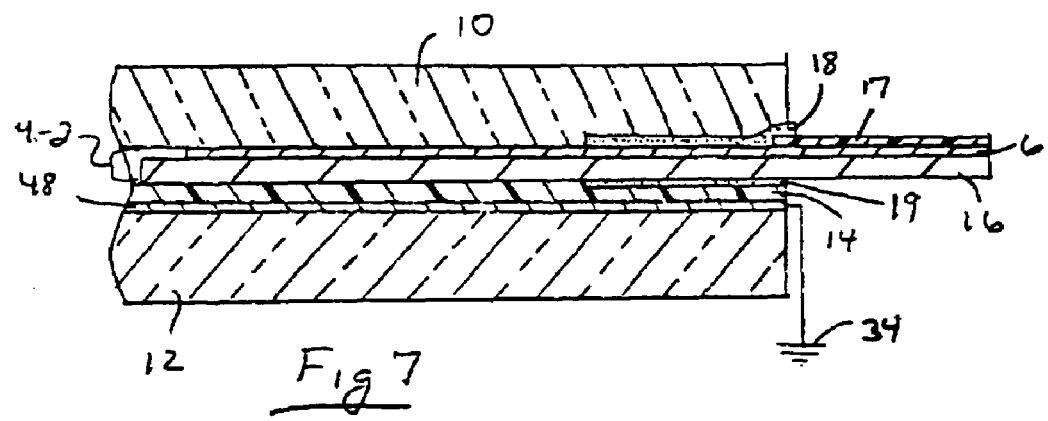
FIG. 7 is a cross section of the second embodiment moisture detector shown in FIG. 4 including an electrically conductive coating on the inside surface of one of the sheets of glass.

With reference to FIG. 7, and with continuing reference to FIGS. 3–6, an electrically conductive coating 48 can also or alternatively be formed on a surface, e.g., inner surface, of glass ply 12 and connected to reference voltage 34 for avoiding undesirable electromagnetic interference from affecting the operation of electrical conductor(s) 6 acting as the resonating element of moisture detector 4-2. Electrically conductive coating 48 can be transparent or colored. When colored, electrically conductive coating 48 can serve the dual purpose of a ground plane or faraday shield for moisture detector 4-2 and a sun shade of windshield 2. While described in connection with the second embodiment moisture detector 4-2, it is to be appreciated that electrically conductive coating 48 can also be disposed on a surface, e.g., inner surface, of glass ply 12 when utilized with the first embodiment moisture detector 4-1 shown in FIGS. 1 and 2. As can be seen, any one or a combination of ground conductor 7, conductive material 46 and/or electrically conductive coating 48 can be utilized for avoiding undesirable electromagnetic interference from affecting the operation of electrical conductor(s) 6 acting as the resonating element of moisture detector 4-2.

Alternatively, substrate 16 can be omitted and one or more of conductor(s) 6 and 7 comprising the second embodiment moisture detector 4-2 can be disposed directly one or more surfaces of glass ply 10, glass ply 12 and/or interlayer 14 in any desired arrangement deemed suitable by one of ordinary skill in the art. Electrically conductive coating 48 can also be utilized in combination with conductor(s) 6 and/or 7 of the second embodiment moisture detector 4-2 when conductor(s) 6 and/or 7 are disposed directly on one or more surfaces of glass ply 10, glass ply 12 and/or interlayer 14.

With reference to FIG. 8, and with continuing reference to FIGS. 1–7, in a third nonlimiting embodiment of the present invention, moisture detector 4-3 includes a first elongated electrical conductor 100 and a second elongated electrical conductor 102 disposed on a flexible substrate 104. Second conductor 102 can at least partially surround first conductor 100 defining a gap 103 between the ends of second conductor 102. A power conductor 106 can also be disposed on substrate 104. Power conductor 106 is electrically connected to first conductor 100 via gap 103 between the ends of second conductor 102. In the particular nonlimiting embodiment illustrated in FIG. 8, conductor 106 is electrically connected to conductor 100 intermediate the ends of conductor 100. A ground conductor 108 can also be disposed on substrate 104. Ground conductor 108 is electrically connected to one end of second conductor 102. Another ground conductor 110 can be disposed on substrate 104 and can be electrically connected to the other end of second conductor 102.

First conductor 100 defines a longitudinal axis 112 and at least the portion of second conductor 102 disposed on a side of first conductor 100 opposite gap 103 defines a longitudinal axis 114 that is positioned in spaced relation with longitudinal axis 112 of first conductor 100. The portions of second conductor 102 on opposite sides of gap 103 also define longitudinal axes 116 and 118 that are positioned in spaced relation with longitudinal axis 112 of first conductor 100. Longitudinal axes 112–118 are shown in phantom in FIG. 8. In the particular nonlimiting embodiment illustrated in FIG. 8, first conductor 100 and second conductor 102 define zigzag paths along their longitudinal axes 112 and 114–118. As used herein, "zigzag" means a series of short, sharp turns or angles resulting in a plurality of distinct points along the path of the conductor. Although not required, these zigzag paths can track each other in substantially spaced relation along their longitudinal axes. Although not required, in the particular embodiment of the moisture detector shown in FIG. 8, longitudinal axes 114, 116 and 118 are substantially parallel to longitudinal axis 112 and the zigzag paths track each other in substantially parallel spaced relation.

It is believed that the zigzag path of the conductors as discussed above increases the sensitivity of the moisture detector by providing multiple electric field emitting points along its length. More specifically, it was observed that a straight conductor element used as a moisture detecting element in one embodiment of the moisture detector of the present invention will have a higher electric field strength at the ends of the element as compared to the electric field strength along its length. By forming the conductors in a zigzag pattern, additional distinct points or tips are formed along its length. At each of these points, the element will have a higher electric field strength as compared to a straight portion of the element, thus creating more sensitive transmitting points in the same overall distance as the straight element. As a result of the more sensitive transmitting points with higher field strength, water drops deposited along the length of the zigzag pattern will cause relatively larger changes in impedance of the moisture detector element and hence would be more detectable in comparison to deposition on the straight line pattern.

Portions 150 and 151 of second conductor 102 spaced from opposite ends of first conductor 100 define longitudinal axes 119 and 120 (shown in phantom), which in the nonlimiting embodiment shown in FIG. 8, are positioned substantially perpendicular to longitudinal axis 112 of first conductor 100. As shown, portions 150 and 151 of second conductor 102 define zigzag paths spaced from the opposite ends of first conductor 100. Although not required, in this particular embodiment portions 119 and 120 are mirror images of each other.

In one nonlimiting embodiment, ground conductor 108 defines a straight line connection to second conductor 102 as shown by the phantom line adjacent ground conductor 108. Optionally, ground conductor 108 at least partially surrounds second conductor 102 as shown in FIG. 8. In the illustrated nonlimiting embodiment of moisture detector 4-3, the optional configuration of ground conductor 108 has a generally rectangular form 152 surrounding second conductor 102. However, this is not to be construed as limiting the invention. The optional configuration of ground conductor 108 defines a gap 121 for passage of power conductor 106 for electrical connection to first conductor 100. Gap 121 is also used for passage of ground conductor 110 for electrical connection to second conductor 102.

Optionally, a temperature sensor 122 is disposed on substrate 104 in close proximity to first and second conductors 100 and 102, respectively. Conductors 124 are connected to temperature sensor 122 to facilitate connection of sensor 122 to suitable sensing circuitry, such as microprocessor 20 described hereinafter.

Substrate 104 of the third embodiment moisture detector 4-3 can be formed from the same material(s) as substrate 16 of the second embodiment moisture detector 4-2. The pattern of conductors 100, 102, 106, 108, 110 and 124 can also be formed on flexible substrate 104 in the manner described in connection with the formation of conductor(s) 6 and 7 on substrate 16 of the second embodiment of moisture detector 4-2. Accordingly, details regarding how the pattern of electrical conductors 100, 102, 106, 108 and 110 and 124 are formed on substrate 104 will not be described herein to avoid unnecessary redundancy.

Third embodiment moisture detector 4-3 including substrate 104 can be sandwiched between glass plies 10 and 12 in the manner discussed above in connection with the second embodiment moisture detector 4-2. Conductive material 46 can be disposed on substrate 104 in the manner described above in connection with moisture detector 4-2 to avoid undesirable electromagnetic interference from affecting the operation of moisture detector 4-3. Similarly, electrically conductive coating 48 can be utilized with the third embodiment moisture detector 4-3 in the manner described above in connection with the second embodiment moisture detector 4-2 including substrate 104.

Alternatively, substrate 104 can be omitted and the conductors comprising the third embodiment moisture detector 4-3 can be disposed directly on one or more surfaces of glass ply 10, glass ply 12 and/or interlayer 14 in any desired arrangement deemed suitable by one of ordinary skill in the art. In one nonlimiting embodiment of the present invention, temperature sensor 122 is disposed on the same surface of glass ply 10, glass ply 12, interlayer 14 or substrate 104 as the conductors of the third embodiment moisture detector 4-3 and positioned adjacent to detector 4-3. Electrically conductive coating 48 can also be utilized with the third embodiment moisture detector 4-3 where the conductors thereof are disposed directly on one or more surfaces of glass ply 10, glass ply 12 and/or interlayer 14.

With reference to FIG. 9, and with continuing reference to FIGS. 1–8, in a fourth nonlimiting embodiment of the present invention, moisture detector 4-4 is similar to the third embodiment moisture detector 4-3 described above except that the fourth embodiment moisture detector 4-4 includes a third conductor 126 disposed on substrate 104 between first conductor 100 and the portion of second conductor 102 having longitudinal axis 114. Fourth embodiment moisture detector 4-4 also includes a fourth conductor 128 disposed on substrate 104 between first conductor 100 and third conductor 126. Fourth conductor 128 defines a gap 130 intermediate the opposite ends of fourth conductor 128 which are coupled to the portions of second conductor 102 having longitudinal axis 119 and 120 associated therewith. Third and fourth conductors 126 and 128 define longitudinal axes 132 and 134, respectively, that are positioned in spaced relation with longitudinal axis 112 of first conductor 100, e.g. in substantially spaced parallel relation. In this nonlimiting embodiment, the portions of second conductor 102 associated with longitudinal axes 114–118 along with conductors 100, 126 and 128 define zigzag paths along their longitudinal axes. These zigzag paths track each other in substantially spaced parallel relation along their longitudinal axes.

Portions of second conductor 102 spaced from opposite ends of first conductor 100 define longitudinal axes 119 and 120 that are positioned substantially perpendicular to longitudinal axis 112 of first conductor 100. The portions of second conductor 102 associated with longitudinal axes 119 and 120 define mirror image zigzag paths.

Power conductor 106 is connected to first conductor 100 intermediate the ends thereof via gap 103 between the ends of second conductor 102. Power conductor 106 is also connected to third conductor 126 intermediate the ends thereof via gap 130 between the ends of fourth conductor 128. Like the third embodiment moisture detector 4-3, ground conductors 108 and 110 are disposed on substrate 104 and are electrically connected to opposite ends of second conductor 102.

In one nonlimiting embodiment of the present invention, temperature sensor 122 is disposed on substrate 104 in operative relation to, for example, second conductor 102.

Fourth embodiment moisture detector 4-4 including substrate 104 can be sandwiched between glass plies 10 and 12 in the manner discussed above in connection with the second embodiment moisture detector 4-2. Although not required, conductive material 46 can be disposed on substrate 104 in the manner described above in connection with moisture detector 4-2 to avoid undesirable electromagnetic interference from affecting the operation of moisture detector 4-4. Similarly, electrically conductive coating 48 can be utilized with the fourth embodiment moisture detector 4-4 including substrate 104 in the manner described above in connection with the second embodiment moisture detector 4-2.

Alternatively, substrate 104 can be omitted and the conductors comprising the fourth embodiment moisture detector 4-4 can be disposed directly on one or more surfaces of glass ply 10, glass ply 12 and/or interlayer 14 in any desired arrangement deemed suitable by one of ordinary skill in the art. In one nonlimiting configuration, temperature sensor 122 is disposed on the same surface of glass ply 10, glass ply 12 or interlayer 14 as the conductors of the fourth embodiment moisture detector 4-4. Electrically conductive coating 48 can also be utilized with the fourth embodiment moisture detector 4-4 where the conductors thereof are disposed directly on one or more surfaces of glass ply 10, glass ply 12 and/or interlayer 14.

Some exemplary dimensions of fourth embodiment moisture detector 4-4 are shown in FIG. 9. These exemplary dimensions are also applicable to the third embodiment moisture detector 4-3. However, these dimensions are not to be construed as limiting the invention.

Figure 10:
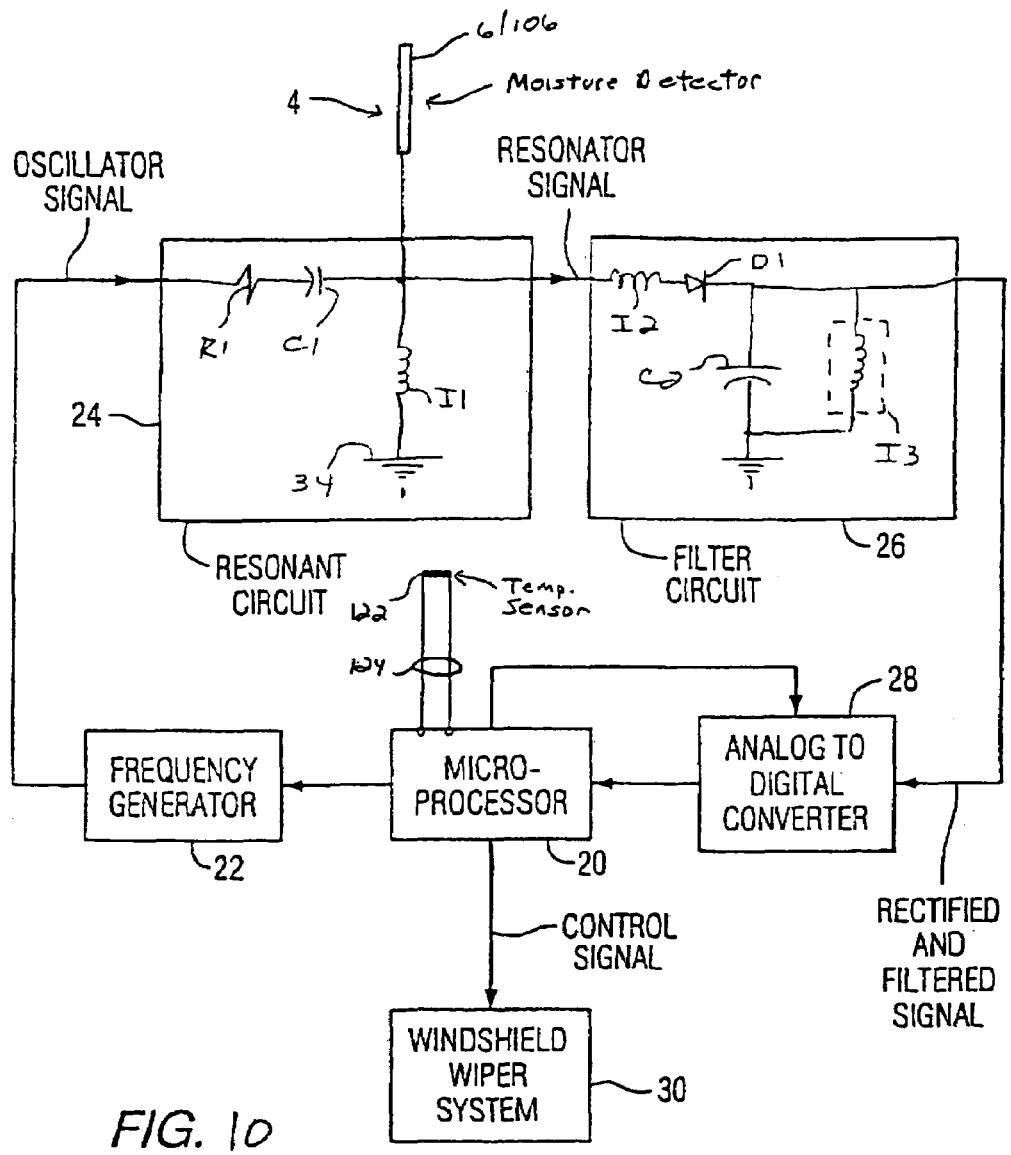
FIG. 10 is a schematic drawing of circuitry utilized to stimulate and detect the response of any one of the first through fourth embodiment moisture detectors.

With reference to FIG. 10, and with continuing reference to all previous figures, the electronic circuitry coupled to electrical conductor 6 of moisture detector 4-1 or 4-2, or to power conductor 106 of moisture detector 4-3 or 4-4 includes a microprocessor 20, a frequency generator 22, a resonant circuit 24, a filter circuit 26, and an analog-to-digital converter 28. A windshield wiper system 30 is connected to receive one or more control signals from microprocessor 20, which control the operation of windshield wiper system 30 in a manner to be described hereinafter.

Microprocessor 20 is interfaced with certain electronic hardware, such as ROM memory, RAM memory, I/O buffers, clock circuitry, and the like, which have not been included in FIG. 10 for simplicity of illustration. Microprocessor 20 operates under the control of a software program stored in a memory connected to microprocessor 20. Under the control of this software program, microprocessor 20 causes frequency generator 22 to output an oscillator signal having a predetermined amplitude and a predetermined frequency. In one nonlimiting embodiment, this predetermined frequency is between 300 kHz and 700 kHz, e.g. between 400 kHz and 600 kHz. The oscillator signal is supplied to resonant circuit 24 which is coupled to electrical conductor 6 of moisture detector 4-1 or 4-2, or to power conductor 106 of moisture detector 4-3 or 4-4. In response to receiving the oscillator signal, resonant circuit 24 outputs a resonator signal to electrical conductor 6 of moisture detector 4-1 or 4-2, or to power conductor 106 of moisture detector 4-3 or 4-4.

In the particular nonlimiting embodiment of the present invention shown in FIG. 10, resonant circuit 24 includes resistor R1, capacitor C1 and choke I1 connected in series as shown. Electrical conductor 6 of moisture 4-1 or 4-2, or power conductor 106 of moisture detector 4-3 or 4-4 is electrically connected to a node between capacitor C1 and choke I1. An inductor I2 is connected between this node and reference voltage 34.

In addition, filter circuit 26 includes a diode D1 connected to conduct the resonator signal from resonant circuit 24 toward analog-to-digital converter 28. A capacitor C2 is connected between a side of diode D1 opposite resonant circuit 24 and reference voltage 34. Optionally, an inductor 13 is connected in parallel with capacitor C2. The output of filter circuit 26 is a rectified and filtered signal that is supplied to digital-to-analog converter 28. Under the control of microprocessor 20, analog-to-digital converter 28 samples the rectified and filtered signal and converts into an equivalent digital signal, which is sampled by microprocessor 20.

In the following description, moisture detector 4 will be utilized. It is to be understood, however, that any one of moisture detectors 4-1 through 4-4 can be substituted for moisture detectors 4.

In order to detect the presence of moisture on windshield 2, microprocessor 20 causes frequency generator 22 to generate the oscillator signal when no moisture is present on an outward facing surface of windshield 2. Microprocessor 20 then determines the response of moisture detector 4 to the oscillator signal by sampling a first digital signal output by analog-to-digital converter 28 when moisture detector 4 is receiving the oscillator signal. Microprocessor 20 stores this first digital signal for future use.

Next, when moisture, e.g., condensed or diffused liquid such as water, is present on the outward facing surface of windshield 2, microprocessor 20 samples a second digital signal output by analog-to-digital converter 28 when moisture detector 4 is receiving the oscillator signal.

Alternatively, microprocessor 20 can sample the first digital signal when moisture e.g., condensed or diffused liquid such as water, is present on the outward facing surface of windshield 2 and can sample the second digital signal when no moisture is present on the outward facing surface of windshield 2. To this end, the first digital signal, corresponding to the presence or absence of moisture on windshield 2, can be utilized as the basis for determining from the second digital signal when moisture is present on or absent from windshield 2. The use of the first and second digital signals to determine the presence or absence of moisture on windshield 2 will be described hereinafter.

It has been observed that the rectified and filtered signal output by filter circuit 26 has a different amplitude when moisture is present on windshield 2 adjacent moisture detector 4. More specifically, the rectified and filtered signal output by filter circuit 26 has an amplitude that increases or decreases to a limit with increasing moisture on windshield 2 adjacent moisture detector 4. For example, in the absence of moisture on windshield 2 adjacent moisture detector 4, the rectified and filtered signal has a first amplitude. However, when moisture in the form of droplets of water is present on windshield 2 adjacent moisture detector 4, the rectified and filtered signal output by filter circuit 26 has a second amplitude different than the first amplitude. Furthermore, when moisture in the form of diffused water is present on windshield 2 adjacent moisture detector 4, the rectified and filtered signal output by filter circuit 26 has a third amplitude different than the second amplitude.

This changing amplitude is caused by the impedance of moisture detector 4, changing due to increasing or decreasing amounts of moisture on windshield 2 adjacent moisture detector 4. More specifically, the impedance of moisture detector 4 decreases in response to increasing amounts of moisture on windshield 2 adjacent moisture detector 4, whereupon the amplitude of the rectified and filtered signal output by filter circuit 26 decreases. Similarly, the impedance of moisture detector 4 increases in response to decreasing amounts of moisture on windshield 2 adjacent moisture detector 4, whereupon the amplitude of the rectified and filtered signal output by filter circuit 26 increases.

The electronic circuitry coupled to moisture detector 4 can detect changes in the impedance thereof due to changes in the moisture on windshield 2 adjacent moisture detector 4 between no moisture and diffused liquid.

Next, microprocessor 20 compares the first digital signal to the second digital signal to determine the amount of moisture that is present on windshield 2 adjacent moisture detector 4. More specifically, microprocessor 20 takes the difference between the first and second digital signals and determines therefrom the presence of moisture, and in one nonlimiting embodiment, an amount of moisture that is present on windshield 2 adjacent moisture detector 4. Based on this determination, microprocessor 20 outputs a control signal to windshield wiper system 30 for controlling the operation thereof based on the amount presence and/or amount of moisture on windshield 2.

Figure 11:
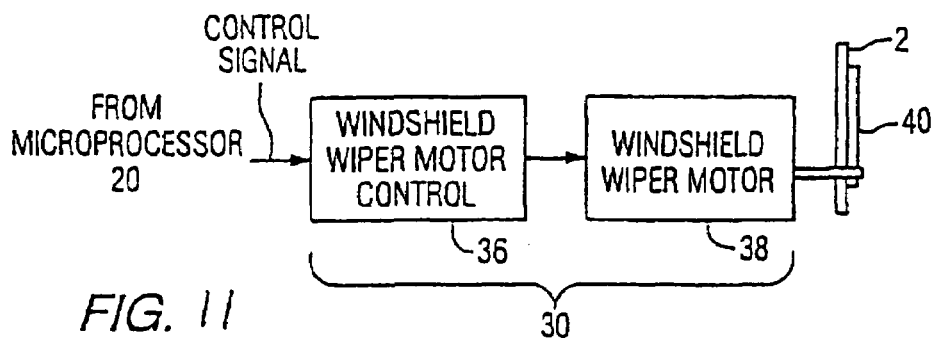
FIG. 11 is a schematic drawing of the windshield wiper system shown in FIG. 10.

With reference to FIG. 11, and with continuing reference to all previous figures, windshield wiper system 30 includes a windshield wiper motor control 36 which receives the control signal from microprocessor 20, and a windshield wiper motor 38 which is coupled to a windshield wiper blade 40 disposed on windshield 2. As discussed above, the control signal supplied by microprocessor 20 to windshield wiper motor control 36 is related to the difference between the first and second digital signals sampled by microprocessor 20. In order to control windshield wiper system 30 in accordance with the amount of moisture on windshield 2 adjacent moisture detector 4, the numerical range of digital difference values that can be processed by microprocessor 20 is divided into sections based on the desired control of windshield wiper system 30. For example, if the range of digital difference values is divided into two sections, the section corresponding to the upper numerical range of difference values corresponds to operating windshield wiper system 30 at a high speed while the lower numerical range of difference values corresponds to operating windshield wiper system 30 at a low speed. Thus, if a difference value between a current sample of the second digital signal and the first digital signal is within the upper numerical range of difference values, microprocessor 20 outputs the control signal which causes windshield wiper motor control 36 to control windshield wiper motor 38 to operate windshield wiper blade 40 at a high speed. Similarly, if the difference value between the current sample of the second digital signal and the first digital signal is within the lower numerical range of difference values, microprocessor 20 outputs the control signal which causes windshield wiper motor control 36 to control windshield wiper motor 38 to operate windshield wiper blade 40 at a low speed.

Various other modes of operation of windshield wiper system 30 can also be enabled by microprocessor 20 and windshield wiper motor control 36 as a function of the difference value between a current sample of the second digital signal and the first digital signal. These modes can include a single pulse mode where windshield wiper blade 40 is caused to wipe windshield 2 once, e.g., to remove dew or mist from windshield 2; a continuous duty cycle pulse mode, e.g., where there is a steady accumulation of water droplets on windshield 2, but the accumulation is not sufficient enough to warrant operation of windshield wiper system 30 at the low speed; and a variable duty cycle pulse mode where wiping of windshield 2 by windshield wiper blade 40 varies as a function of the amount and/or rate of moisture accumulation on windshield 2.

Microprocessor 20 can be configured to output two or more different control signals which cause windshield wiper system 30 to implement two or more of the above modes of operation in response to varying amounts of moisture on windshield 2. In the absence of moisture on windshield 2, microprocessor 20 can cause windshield wiper system 30 to either discontinue or not initiate the wiping of windshield 2 with windshield wiper blade 40.

It has been observed that the temperature of windshield 2 can affect the sensitivity of each embodiment moisture detector 4 discussed above. Accordingly, a temperature sensor, like temperature sensor 122 described above, can be disposed in operative relation to the corresponding moisture detector 4 or on flexible substrate 16 or 104 disposed on windshield 2, e.g. on one of the surfaces of glass ply 10, glass ply 12, plastic interlayer 14 or flexible substrates 16 or 104, in order to detect the temperature of windshield 2 at or adjacent moisture detector 4.

In operation, microprocessor 20 determines the response of moisture detector 4 to the oscillator signal output by frequency generator 22 by sampling one or more digital signals output by analog-to-digital converter 28 when moisture detector 4 is receiving the oscillator signal. On or about the time microprocessor 20 samples each digital signal output by analog-to-digital converter 28, microprocessor 20 measures a property of temperature sensor 122 that varies in response to the temperature at or adjacent temperature sensor 122. As a function of this measured property, microprocessor 20 applies a correction factor to each digital signal received by microprocessor 20 from analog-to-digital converter 28. The correction factor applied to each digital signal received by microprocessor 20 adjusts the value of the digital signal based on the measured temperature at or adjacent moisture detector 4, whereupon the control signal output by microprocessor 20 to windshield wiper system 30 is adjusted for temperature, thereby avoiding inadvertent operation or non-operation of windshield wiper system 30. Thus, windshield wiper system 30 is operated as a function of the measured properties of moisture detector 4 and temperature sensor 122.

In one nonlimiting embodiment, temperature sensor 122 is a thermistor that has a resistance that changes as a function of the temperature. Alternatively, temperature sensor 122 can be a bimetallic junction temperature sensor, or a conductor having a resistance that changes as a function of the temperature, or an optical temperature sensor that optically detects the temperature of windshield 2 on or adjacent moisture detector 4 by optical means, and which outputs to microprocessor 20 a signal indicative of the thus detected temperature.

Figure 12A:
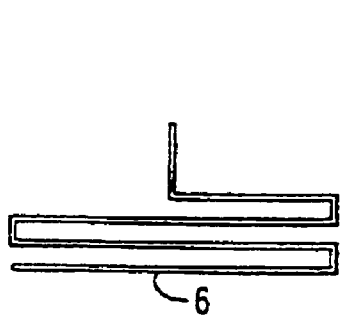
FIGS. 12a–12d show alternate embodiments of the electrical conductor of the first and second embodiment moisture detectors.
Figure 12B:
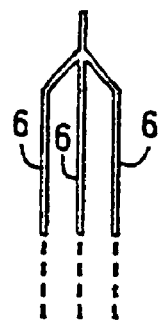
Figure 12C:
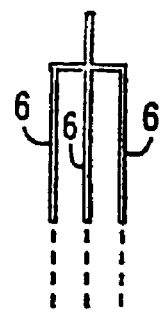
Figure 12D:
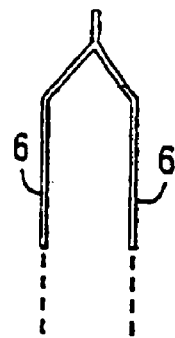

With reference to FIGS. 12a–12d, various different embodiments of electrical conductor 6 of the first and second embodiments of moisture detectors 4-1 and 4-2 are illustrated. FIG. 12a and FIG. 5 show electrical conductor 6 formed in a serpentine pattern. FIGS. 12b and 12c show three parallel electrical conductors 6 extending in spaced relation from a common junction. As indicated by the dashed extensions of electrical conductors 6 in FIGS. 12b and 12c, electrical conductors 6 can be formed to any desired length. Lastly, in FIG. 12d, two parallel electrical conductors 6 extend in spaced relation from a common junction. Again, the dash lines extending from electrical conductors 6 in FIG. 12d indicate that electrical conductors 6 can have any desired length.

The present invention has several advantages over prior art systems for detecting moisture. These advantages include moisture detector 4 being essentially invisible to the naked eye from about one meter; moisture detector 4 can be disposed in a clear or non-transparent part of windshield 2; moisture detector 4 is not sensitive to dirt; moisture detector 4 can detect the presence of moisture over a larger area than prior art sensors of comparable size; moisture detector 4 is useful with substrates of various thickness and composition; moisture detector 4 is more uniformly responsive than prior art sensors; and the present invention can detect the presence of moisture droplets of smaller size, e.g., dew or mist, on windshield 2 than the prior art systems for detecting moisture.

Figure 13:
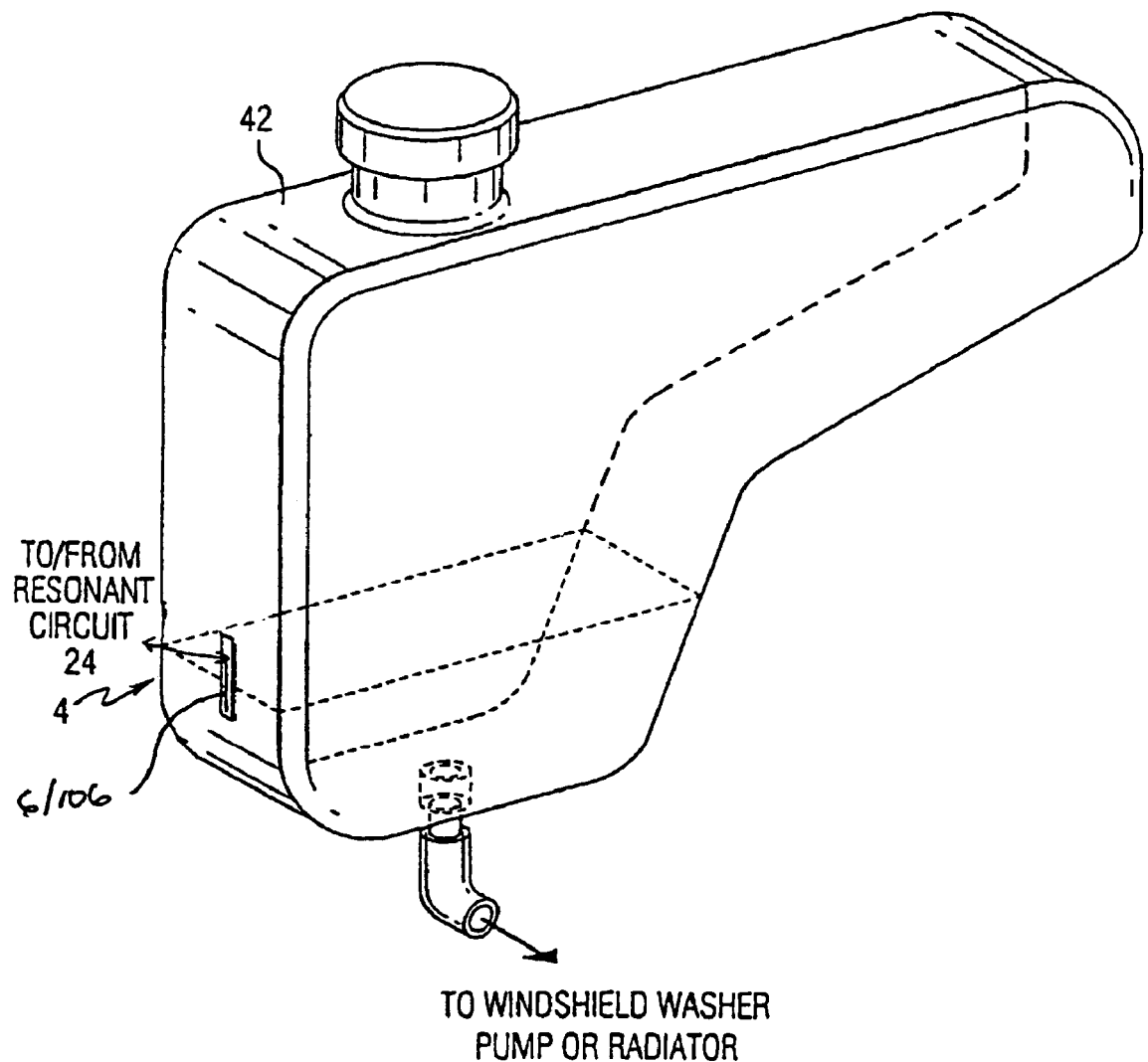
FIG. 13 is an isolated perspective view of a fluid reservoir of a vehicle including any one of the first through fourth embodiment moisture detectors disposed thereon.

With reference to FIG. 13 and with reference back to FIG. 10, the present invention can also be utilized to detect a level of one or more fluids, such as the level of a fluid in a vehicle. Specifically, moisture detector 4 can be mounted on an electrically and magnetically nonconductive fluid reservoir 42. Preferably, moisture detector 4 is mounted on an exterior of fluid reservoir 42 adjacent a lower end thereof. However, this is not to be construed as limiting the invention. Fluid reservoir 42 can be configured to receive windshield washer fluid, radiator fluid, or any other fluid utilized by a vehicle, the level of which fluid can be measured utilizing moisture detector 4 and the electronic circuitry shown in FIG. 10.

In order to detect the level of fluid in fluid reservoir 42, the oscillator signal is supplied to electrical conductor 6 or 106 of moisture detector 4 when no fluid is received in fluid reservoir 42. A first response of moisture detector 4 is sampled and stored for later use. At suitable times when fluid is received in the fluid reservoir, plural second responses of moisture detector 4 to the oscillator signal are sampled. Each second response is compared to the first response. When a second response has a predetermined relation to the first response, the electronic circuitry outputs a corresponding control signal which activates a suitable indicator, e.g., "check washer fluid", "check radiator fluid", etc.

It is to be appreciated that decreasing the fluid level in fluid reservoir 42 decreases the difference between the first response and the second response of moisture detector 4. Thus, when the second response has the predetermined relation to the first response indicative of the fluid level decreasing to a predetermined level, the electronic circuitry outputs the control signal. To facilitate detecting the change in the resonant frequency of moisture detector 4, the predetermined frequency of the oscillator signal can be selected to optimize the change in impedance of moisture detector 4 in response to the presence of fluid in fluid reservoir 42. Similar comments apply in respect of the change in resonant frequency of moisture detector 4 due to the presence of moisture on windshield 2.

When a vehicle includes multiple moisture detectors 4, a multiplexer (not shown) can be connected between each moisture detector 4 and the electronic circuitry shown in FIG. 10. Under the control of microprocessor 20, the multiplexer can selectively connect the electronic circuitry to each moisture detector 4 for supplying the oscillator signal at an appropriate frequency to each moisture detector 4 and for detecting the response of each moisture detector 4 to the supplied oscillator signal. Preferably, under the control of the software program, microprocessor 20 can adjust the frequency of the oscillator signal output by frequency generator 22 to optimize the change in the resonant frequency of each moisture detector 4 to detect the presence or absence of a particular fluid.

The invention has been described with reference to several nonlimiting embodiments. Obvious modifications and alterations will occur to others upon reading and understanding the preceding detailed description. For example, while described in connection with the detection of moisture on windshield 2, the present invention can also be utilized to detect moisture on surfaces of rigid or flexible substrates utilized in connection with other applications. Similarly, while described in connection with detection of fluid levels in a fluid reservoir 42 mounted on a vehicle, the present invention can also be utilized to detect the level of a fluid received in a fluid reservoir utilized in other applications. Moreover, while described in connection with the control of windshield wiper system 30, microprocessor 20 can also be utilized to control a vehicle headlamp system, a vehicle windshield dehumidification system and/or any other vehicle or non-vehicle based system that it is desired to control as a function of the presence of moisture on a substrate. Still further, while the various components of the electronic circuitry are preferably connected by conductors, it should be appreciated that suitable signals can be conveyed between two or more of these components via suitable radio frequency (RF) and/or optical signal means. Microprocessor 20 can also be configured to record for subsequent retrieval and display, the days when moisture is detected on a substrate and/or the extent of operation of windshield wiper system 30. This information can then be used for information purposes, e.g., to determine the number of days in a month it rains, and/or to estimate when blades of the windshield wiper system 30 may require replacement. It is intended that the invention be construed as including all such modifications and alterations insofar as they come within the scope of the appended claims or the equivalents thereof.

The invention claimed is:

1. A moisture detector comprising:
   a first elongated conductor disposed on a substrate, the first conductor defining a path comprising multiple electric field emitting points between opposite ends thereof; and
   a second elongated conductor disposed on the substrate at least partially surrounding the first conductor, the second conductor defining between opposite ends thereof a path having portions thereof which are positioned in spaced relation with the path of the first conductor along opposite sides thereof and a portion spaced from one of the ends of the first conductor for connecting the portions of the second conductor in spaced relation with the path of the first conductor along the opposite sides thereof.

2. The moisture detector of claim 1, wherein the path of the first conductor is a zigzag path and the path of the second conductor is a zigzag path positioned in substantially parallel spaced relation with the zigzag path of the first conductor.

3. The moisture detector of claim 1, further comprising:
   a power conductor disposed on the substrate and electrically connected to the first conductor; and
   a ground conductor disposed on the substrate and electrically connected to one end of the second conductor.

4. The moisture detector of claim 3, wherein the power conductor is electrically connected to the first conductor intermediate the ends thereof via a gap defined between the ends of the second conductor.

5. The moisture detector of claim 3, further comprising another ground conductor disposed on the substrate and electrically to the other end of the second conductor.

6. The moisture detector of claim 3, wherein the ground conductor at least partially surrounds the second conductor.

7. The moisture detector of claim 6, wherein the ground conductor defines a gap for passage of the power conductor for electrical connection to the first conductor.

8. The moisture detector of claim 1, further comprising:
   a third elongated conductor disposed on the substrate between the first and second conductors, the third conductor defining between opposite ends thereof a path that is positioned in spaced relation with the path of the first conductor; and
   a fourth elongated conductor disposed on the substrate between the first and third conductors, the fourth conductor defining between opposite ends thereof a path that is positioned in spaced relation with the path of the first conductor, the fourth conductor defining a gap intermediate the ends thereof which are coupled to the second conductor.

9. The moisture detector of claim 8, wherein the path of the first conductor is a zigzag path, the path of the second conductor is a zigzag path positioned in substantially parallel spaced relation with the zigzag path of the first conductor, the path of the third conductor is a zigzag path positioned in substantially spaced parallel relation with the zigzag path of the first conductor, and the path of the fourth conductor is a zigzag path positioned in substantially parallel spaced relation with the zigzag path of the first conductor.

10. The moisture detector of claim 8, further comprising:
    a power conductor disposed on the substrate and electrically connected to the first conductor, the power conductor electrically connected to the third conductor; and
    a ground conductor disposed on the substrate and electrically connected to one end of the second conductor.

11. The moisture detector of claim 10, wherein the power conductor is electrically connected to the first conductor intermediate the ends thereof via a gap defined between the ends of the second conductor, and the power conductor is electrically connected to the third conductor intermediate the ends thereof via the gap defined intermediate the ends of the fourth conductor.

12. The moisture detector of claim 11, wherein the path of the first conductor is a zigzag path, the path of the second conductor is a zigzag path positioned in substantially parallel spaced relation with the zigzag path of the first conductor, the path of the third conductor is a zigzag path positioned in substantially spaced parallel relation with the zigzag path of the first conductor, and the path of the fourth conductor is a zigzag path positioned in substantially parallel; spaced relation with the zigzag path of the first conductor.

13. The moisture detector of claim 10, further comprising another ground conductor disposed on the substrate and electrically connected to the other end of the second conductor.

14. The moisture detector of claim 10, wherein the ground conductor at least partially surrounds the second conductor.

15. The moisture detector of claim 14, wherein the ground conductor defines a gap for passage of the power conductor for electrical connection to the first and third conductors.

16. The moisture detector of claim 1, wherein the substrate is one of:
    a laminate having a plurality of transparent sheets laminated together; and
    a flexible substrate configured to be disposed between transparent sheets of a laminate.

17. The moisture detector of claim 1, further comprising a temperature sensor disposed in operative relation to the conductors.

18. A moisture detector comprising:
    a first conductor disposed on a substrate;
    a second conductor disposed on the substrate surrounding the first conductor with a gap defined between the ends of the second conductor;
    a power conductor disposed on the substrate and electrically connected to the first conductor via the gap between the ends of the second conductor; and
    a ground conductor disposed on the substrate and electrically connected to one end of the second conductor.

19. The moisture detector of claim 18, wherein:
    the first conductor defines a longitudinal axis; and
    at least a portion of the second conductor defines a longitudinal axis that is positioned in spaced relation with the longitudinal axis of the first conductor.

20. The moisture detector of claim 19, wherein the longitudinal axis of the second conductor is positioned in substantially spaced parallel relation with the longitudinal axis of the first conductor.

21. The moisture detector of claim 20, wherein the first conductor defines a path comprising multiple electric field emitting points between opposite ends thereof.

22. The moisture detector of claim 21, wherein:
    the first and second conductors define zigzag paths along their longitudinal axes; and
    the zigzag paths of the first and second conductors track each other in substantially spaced parallel relation along their longitudinal axes.

23. The moisture detector of claim 22, wherein:
portions of the second conductor spaced from opposite ends of the first conductor define longitudinal axes that are positioned substantially perpendicular to the longitudinal axis of the first conductor; and
the portions of the second conductor define zigzag paths.

24. The moisture detector of claim 18, wherein the ground conductor at least partially surrounds the second conductor.

25. The moisture detector of claim 24, wherein the ground conductor defines a gap for passage of the power conductor for electrical connection to the first conductor.

26. The moisture detector of claim 18, further comprising:
a third conductor disposed on the substrate between the first and second conductors; and
a fourth conductor disposed on the substrate between the first and third conductors, the fourth conductor defining a gap intermediate the opposite ends thereof which are coupled to the second conductor, wherein the power conductor is electrically connected to the third conductor via the gap intermediate the ends of the fourth conductor.

27. The moisture detector of claim 26, wherein:
the first conductor defines a longitudinal axis;
at least a portion of the second conductor defines a longitudinal axis that is positioned in substantially spaced parallel relation with the longitudinal axis of the first conductor; and
the third and fourth conductors define longitudinal axes that are positioned in substantially spaced parallel relation with the longitudinal axis of the first conductor.

28. The moisture detector of claim 26, wherein at least one of the first and third conductors defines a path comprising multiple electric field emitting points between opposite ends thereof.

29. The moisture detector of claim 28, wherein:
the conductors define zigzag paths along their longitudinal axes; and
the zigzag paths of the conductors track each other in substantially spaced parallel relation along their longitudinal axes.

30. The moisture detector of claim 26, wherein the ground conductor at least partially surrounds the second conductor.

31. The moisture detector of claim 30, wherein the ground conductor defines a gap for passage of the power conductor for electrical connection to the first and third conductors.

32. The moisture detector of claim 18, wherein the substrate is one of:
a laminate having a plurality of transparent sheets laminated together; and
a flexible substrate configured to be disposed between transparent sheets of a laminate.

33. The moisture detector of claim 18, further including a temperature sensor disposed in operative relation to the conductors.

34. A moisture detection system comprising:
a moisture detector disposed on a substrate, said moisture detector comprising at least one conductor that has a zigzag path along a longitudinal axis of said conductor and an other conductor surrounding the one conductor with a gap defined between the ends of the other conductor;
a temperature sensor disposed in operative relation to the moisture detector for measuring a temperature on or adjacent the moisture detector;
means for measuring a property of the moisture detector that varies in response to an amount of moisture present adjacent the moisture detector;
means for measuring a property of the temperature sensor that varies in response to the temperature adjacent the moisture detector; and
means for causing a system to operate as a function of the measured properties of the moisture detector and the temperature sensor.

35. The moisture detection system of claim 34, wherein:
the substrate is a windshield; and
the system is a windshield wiper system.

36. The moisture detection system of claim 34, wherein the measured property of the temperature sensor is one of:
a potential output by a bimetallic junction acting as the temperature sensor;
a resistance of a thermistor or a conductor acting as the temperature sensor; and
a signal output by an optical temperature sensor acting as the temperature sensor.

37. A moisture detector comprising:
a plurality of conductors disposed on a substrate and defining along their longitudinal axes zigzag paths that track each other in substantially spaced parallel relation, wherein each zigzag path includes a series of short, sharp turns or angles that define a series of distinct points;
a power conductor disposed on the substrate and electrically connected to a first conductor of the plurality of conductors; and
a ground conductor disposed on the substrate and electrically connected to a second conductor of the plurality of conductors wherein:
the second conductor of the plurality of conductors surrounds the remaining plurality of conductors and defines a gap between the ends of the second conductor; and
the power conductor is electrically connected to the first conductor via the gap between the ends of the second conductor.

38. The moisture detector of claim 37, wherein:
portions of the second conductor spaced from opposite ends of the first conductor define longitudinal axes that are positioned substantially perpendicular to the longitudinal axis of the first conductor; and
the portions of the second conductor define mirror image zigzag paths.

39. The moisture detector of claim 37, wherein:
a third conductor of the plurality of conductors is positioned between the first and second conductors;
a fourth conductor of the plurality of conductors is positioned between the first and third conductors;
the fourth conductor defines a gap intermediate the ends thereof which are electrically connected to the ground conductor; and
the power conductor is electrically connected to the third conductor via the gap intermediate the ends of the fourth conductor.

40. The moisture detector of claim 37, wherein the substrate is one of:
a windshield having a plurality of transparent sheets laminated together; and
a flexible substrate configured to be disposed between the transparent sheets of a laminated windshield.

41. The moisture detector of claim 37, further including a temperature sensor disposed in operative relation to the plurality of conductors.

42. A method of moisture detection comprising:
(a) providing a moisture detector on a substrate, said moisture detector comprising a conductor that has a zigzag path along a longitudinal axis of said conductor;
(b) providing a temperature sensor in operative relation to the moisture detector;
(c) measuring a property of the moisture detector that varies in response to an amount of moisture present adjacent the moisture detector;
(d) measuring a property of the temperature sensor that varies in response to the temperature adjacent the moisture detector; and
(e) causing a system to operate as a function of the measured properties of the moisture detector and the temperature sensor.

43. A moisture detector comprising:
a first elongated conductor disposed on a substrate, the first conductor defining a path comprising multiple electric field emitting points between opposite ends thereof; and
a second elongated conductor disposed on the substrate at least partially surrounding the first conductor, the second conductor defining between opposite ends thereof a path having a portion thereof which is positioned in spaced relation with the path of the first conductor along the sides thereof, wherein the path of the first conductor is a zigzag path that includes a series of short, sharp turns or angles that define a series of distinct points, each of which defines one of the electric field emitting points.

* * * * *